United States Patent [19]
Brannon

[11] Patent Number: 6,013,037
[45] Date of Patent: Jan. 11, 2000

[54] SYRINGE WITH CONDUIT

[75] Inventor: James K. Brannon, Culver City, Calif.

[73] Assignee: Vascular Logics, Inc., Huntington Beach, Calif.

[21] Appl. No.: 08/987,258

[22] Filed: Dec. 9, 1997

Related U.S. Application Data

[63] Continuation-in-part of application No. 08/797,091, Feb. 7, 1997, Pat. No. 5,873,841.

[51] Int. Cl.⁷ ........................................................ A61B 5/00
[52] U.S. Cl. ............................................................ 600/576
[58] Field of Search .................................... 600/576, 577, 600/583; 604/187, 131, 239

[56] References Cited

U.S. PATENT DOCUMENTS

| | | |
|---|---|---|
| 701,671 | 6/1902 | Billings . |
| 1,272,742 | 7/1918 | Weguelin . |
| 1,410,530 | 3/1922 | Larche . |
| 2,073,067 | 11/1936 | Klein et al. . |
| 3,064,648 | 11/1962 | Bujan . |
| 3,931,815 | 1/1976 | Takatsuki . |
| 4,150,666 | 4/1979 | Brush . |
| 4,274,408 | 6/1981 | Nimrod . |
| 4,312,362 | 1/1982 | Kaufman ................................ 128/763 |
| 4,378,812 | 4/1983 | Sarstedt . |
| 4,412,832 | 11/1983 | Kling et al. . |
| 4,660,569 | 4/1987 | Etherington ............................ 128/765 |
| 4,813,938 | 3/1989 | Raulerson . |
| 4,936,315 | 6/1990 | Lineback . |
| 5,045,062 | 9/1991 | Raulerson . |
| 5,125,414 | 6/1992 | Dysarz . |
| 5,133,362 | 7/1992 | Moss . |
| 5,147,329 | 9/1992 | Brannon .................................. 604/231 |
| 5,324,267 | 6/1994 | Ambrisco et al. . |
| 5,474,546 | 12/1995 | Ambrisco et al. . |

FOREIGN PATENT DOCUMENTS

| | | |
|---|---|---|
| WO 88/03778 | 2/1988 | European Pat. Off. . |
| 3025800 A1 | 4/1982 | Germany . |

*Primary Examiner*—Max Hindenburg
*Attorney, Agent, or Firm*—Lyon & Lyon LLP

[57] ABSTRACT

A medical syringe for collecting blood samples, including a cylindrical body having an open proximal end, a closed distal end, and a distal opening. A plunger assembly has a distal portion that is slidably disposed in the proximal end of the cylindrical body, thereby defining a fluid chamber between the distal portion and the distal end of the cylindrical body. The plunger assembly has a proximal portion with a cavity therein. A conduit extends from the fluid chamber proximally through the distal portion to the cavity. A penetrable seal, such as a multi-sample luer adapter, is fixed in the cavity, thereby sealing the conduit from retrograde flow of air. Fluid may be drawn into the fluid chamber, a vacuum specimen tube may be inserted into the cavity, and the penetrable seal penetrated to provide fluid-tight communication between the conduit and the specimen tube, fluid being preferentially drawn into the specimen tube from the fluid chamber. Alternatively, the syringe may include a cannula extending between the distal opening and the conduit, through which fluid may flow substantially separately from fluid in the fluid chamber.

21 Claims, 3 Drawing Sheets

SYRINGE WITH CONDUIT

This application is a continuation-in-part of application Ser. No. 08/797,091, filed Feb. 7, 1997, now U.S. Pat. No. 5,873,841 the disclosure of which is expressly incorporated herein by reference.

FIELD OF THE INVENTION

The present invention relates generally to medical syringes for withdrawing fluid from a patient, and more particularly to a syringe for collecting multiple samples of blood for laboratory testing that substantially minimizes contamination of and/or hemolysis in the samples.

BACKGROUND

Many conventional devices are available for obtaining blood samples from a patient for laboratory testing. For example, a conventional syringe and hypodermic needle are often used to draw blood from a patient. A conventional syringe, however, may not facilitate taking multiple samples, since it may require multiple percutaneous introductions into the patient. Alternatively, a single fluid sample may be obtained using the syringe which may then be injected into individual specimen tubes, but this may increase the risk of contamination and/or accidental needle sticks.

Instead, when multiple samples are needed for laboratory tests, a blood collection needle is often used. Generally, such devices include a pair of needles disposed in line axially on a central hub or housing which are provided as part of a tube-holding device. The tube-holding device is typically a hollow cylindrical body with an open end and with the hub of the blood collection needle generally attached to the other end such that one needle extends into the cylindrical body, while the other needle extends axially beyond the cylindrical body for percutaneous introduction into a patient.

Conventional vacuum specimen tubes may then be inserted into the open end of the cylindrical body. The rubber stopper of the specimen tube is punctured by the needle inside the cylindrical body, creating a continuous passage from the percutaneous needle tip to the specimen tube. Thus, after the tube-holding device has been introduced into a patient, a series of vacuum specimen tubes may be successively inserted into it to collect samples for testing.

One of the problems often encountered when such devices are used is hemolysis. When the specimen tube is inserted into the tube-holding device, the fixed vacuum of the specimen tube may draw blood quickly through the needles. The uncontrolled flow of blood caused by the force of this vacuum may cause red blood cells to shear and break down. Potassium may be released from the cells into the blood fluid, creating inaccuracies in the laboratory tests performed on the samples.

Additionally, such conventional devices may present problems in obtaining samples from patients having poor peripheral access, such as young and elderly patients whose veins are smaller or more susceptible to collapse. Vein patency, that is, whether a vein can provide a desired volume of blood for the needed samples, is often a concern, particularly when a vein is subjected to an uncontrollable vacuum or blood flow, as may occur when multiple vacuum specimen tubes are used to obtain samples.

Attempts have been made to modify these conventional blood collection devices to respond to these problems. For example, U.S. Pat. No. 5,133,362, issued to Moss, discloses a blood collection needle which uses a smaller gauge needle for introduction into the patient than is used for the specimen tubes. The device uses such smaller gauge needles to provide improved peripheral access, while also intending to slow blood flow through the needles to reduce hemolysis. This device, however, may not properly address the viscous effects of blood flow through the needles, which contributes substantially to hemolysis in the resulting blood samples.

Thus, there is a need for an apparatus for drawing blood from a patient which substantially reduces the risk of hemolysis as blood is drawn into vacuum specimen tubes.

There is also a need for an apparatus for drawing multiple blood samples for laboratory testing which minimizes contamination and thereby improves the accuracy of test results.

SUMMARY OF THE INVENTION

The present invention is directed towards a syringe for collecting a fluid sample, preferably a plurality of blood samples, from a patient, either percutaneously or from an indwelling catheter. Generally, the syringe includes a cylindrical body and a plunger assembly. The cylindrical body has an interior wall, an open proximal end, a closed distal end, and a distal opening through the distal end. A hypodermic needle may be provided on the distal end communicating with the distal opening, or an indwelling catheter may be attached to a hub on the distal end.

The plunger assembly has proximal and distal ends, and proximal and distal portions. The distal portion is substantially narrow and is slidably disposed in the proximal end of the cylindrical body. A piston on the distal end sealably engages the interior wall, thereby defining a fluid chamber between a piston face on the piston and the distal end of the cylindrical body. The proximal portion includes a cavity therein for receiving a vacuum specimen tube. A conduit extends proximally from the fluid chamber through the distal portion of the plunger assembly to a proximal opening in the cavity in the proximal portion. The conduit is preferably substantially narrow, and may be uniform or tapered along its length.

Finally, a penetrable seal is provided in the cavity for substantially sealing the conduit from retrograde flow of air and for engaging a specimen tube. Preferably, the penetrable seal is a multi-sample luer adapter sealably attached to the proximal opening. The multi-sample luer adapter includes a hub that may be at least partially disposed through the proximal opening into the conduit to secure the multi-sample luer adapter and/or to substantially seal the conduit. The multi-sample luer adapter includes a needle attached to the hub which extends from the proximal opening into the cavity. A rubber seal substantially covers the needle, the needle and rubber seal together providing the penetrable seal.

The syringe may be used to obtain one or more blood samples for laboratory testing. The syringe may be percutaneously introduced into a patient, and the plunger assembly may be drawn proximally to draw fluid into the fluid chamber. A vacuum specimen tube may be inserted into the cavity to obtain a blood sample, causing the needle to penetrate the rubber seal and a stopper on the specimen tube to sealably connect the interior of the specimen tube to the conduit, and thereby draw fluid through the conduit into the specimen tube.

The present invention substantially avoids the problems associated with conventional blood collection needles caused by the exposure of fluid, such as blood, to the uncontrollable initial low pressure of the specimen tube. The fluid chamber of the syringe provides a reservoir from which fluid may be preferentially drawn to prevent hemolysis which may result from uncontrolled flow through the hypodermic needle.

When the vacuum specimen tube is first inserted into the cavity, the blood within the syringe is exposed to the fixed initial low pressure in the specimen tube. Because the hypodermic needle or an indwelling catheter on the distal end may have a relatively high viscous resistance to blood flow as compared to the conduit, blood may be preferentially drawn from the fluid chamber, decelerating the proximal movement of the plunger assembly. Thus, blood flow is controlled more precisely under the fixed pressure of the specimen tube using the present invention, thereby substantially reducing the likelihood of hemolysis within the sample obtained. Furthermore, the syringe allows a smaller gauge hypodermic needle to be attached to the hub, without substantially increasing the risk of hemolysis.

Thus, it is an object of the present invention to provide a syringe for obtaining one or more fluid samples, the syringe remaining substantially sealed throughout its use, thereby minimizing exposure of the fluid therein to air or other contaminants.

It is also an object to provide a syringe for obtaining blood samples which is easily manipulated during its use and which minimizes hemolysis in the samples.

Other objects and features of the present invention will become apparent from consideration of the following description taken in conjunction with the accompanying drawings.

BRIEF DESCRIPTION OF THE DRAWINGS

For a better understanding of the invention, and to show how it may be carried into effect, reference will be made, by way of example, to the accompanying drawings, in which.

DESCRIPTION OF THE PREFERRED EMBODIMENTS

Figure 1:
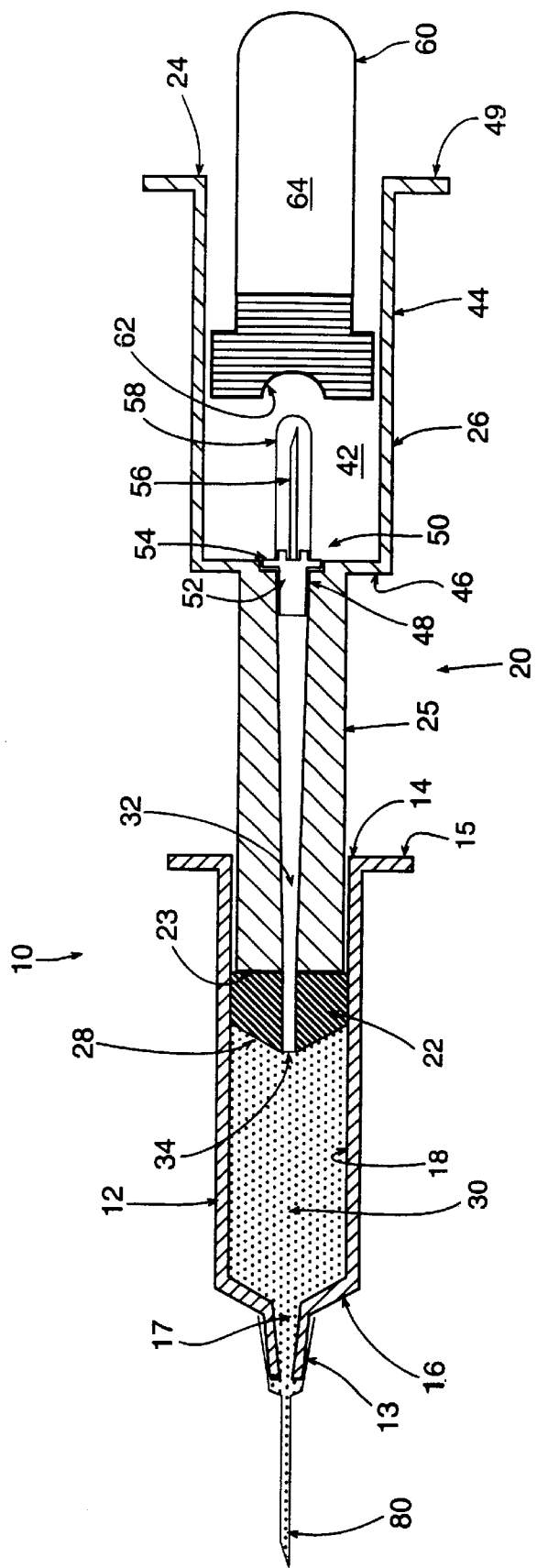
FIG. 1 is a cross-section of a first preferred embodiment of a syringe in accordance with the present invention, with a vacuum specimen tube being inserted into a tube-receiving cavity in its proximal end.
Figure 2:
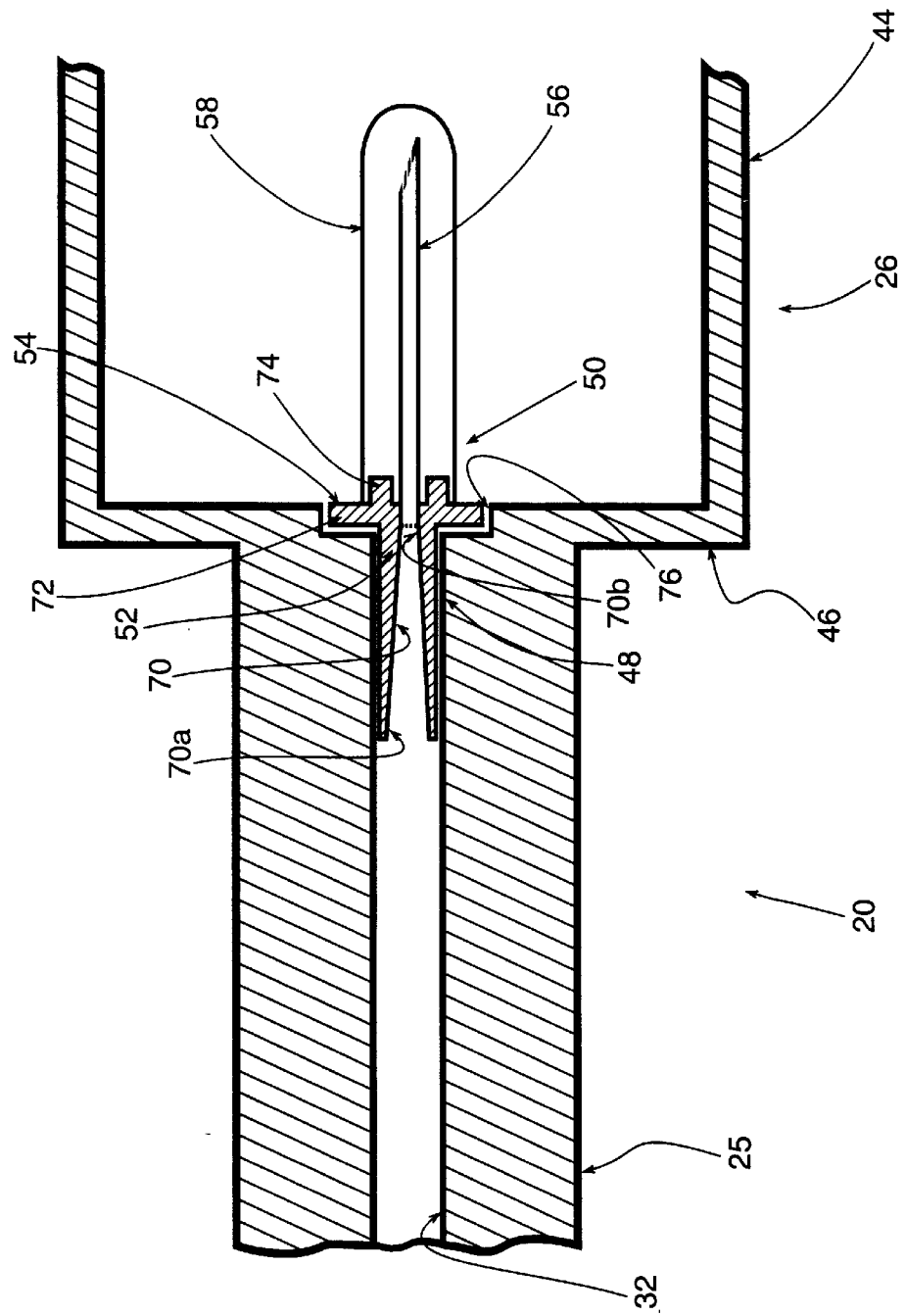
FIG. 2 is a detail of a multi-sample luer adapter and plunger assembly of the syringe of FIG. 1.

Turning to the drawings, FIGS. 1 and 2 show a first preferred embodiment of a syringe 10 in accordance with the present invention. The syringe 10 includes a substantially cylindrical body 12, having an open proximal end 14 and a closed distal end 16. A finger grip 15 extends radially outward from the proximal end 14, such as a pair of flanges or a ring, which are preferably directly formed on the cylindrical body 12.

A hub 13 extends distally from the distal end 16 of the cylindrical body 12, preferably being integrally formed thereon. The hub 13 has a distal opening 17 extending distally therethrough and has a shape adapted to detachably or permanently receive a hypodermic needle 80 thereon, although alternatively the hub 17 may include a configuration for receiving an indwelling catheter, such as a threaded bore or collar (not shown).

The syringe 10 also includes a unitary plunger assembly 20, having a distal end 23 and a proximal end 24, and having an elongate distal portion 25 and an enlarged proximal portion 26. The distal portion 25 is slidably disposed in the open proximal end 14 of the cylindrical body, and preferably has a substantially narrow cross-section. A piston 22 is attached to the distal portion 23 on the distal end 24 of the plunger assembly 20 which sealably engages an interior wall 18 of the cylindrical body 12, thereby defining a fluid chamber 30 between a piston face 28 and the distal end 16 of the cylindrical body 12. Preferably, the distal portion 25 also includes axial ribs (not shown) for substantially minimizing lateral movement of the proximal portion 25 within the cylindrical body 12.

A conduit 32 extends proximally from an opening 34 in the piston face 28 through the distal portion 25, thereby providing passage between the fluid chamber 30 and the proximal portion 26 of the plunger assembly 20. The conduit 32 is preferably formed directly in the distal portion 25, and has a substantially narrow diameter, thereby minimizing the volume of the conduit, and may be substantially uniform or tapered (as shown) along its length.

The enlarged proximal portion 26 of the plunger assembly 20 extends proximally beyond the finger grip 15 on the cylindrical body 12, and preferably has a substantially cylindrical shape. The proximal end 24 includes a finger grip 49 which extends radially outward, similar to the finger grip 15 on the cylindrical body 12.

A tube-receiving cavity 42 extends distally into the proximal portion 26 from the proximal end 24, and the proximal portion 26 has a side wall 44 and an end wall 46 therein. Preferably, the tube-receiving cavity 42 has a substantially cylindrical shape and a diameter corresponding substantially to a vacuum specimen tube 60. A proximal opening 48 extends through the end wall 46, thereby providing communication between the tube-receiving cavity 42 and the conduit 32.

With particular reference to FIG. 2, a multi-sample luer adapter 50 is coupled to the end wall 46, preferably in the proximal opening 48. The multi-sample luer adapter 50 includes a distal hub 52, a proximal hub 54, and a needle 56 which extends proximally from the proximal hub 54. A substantially resilient rubber seal 58 is also sealably attached to the proximal hub 54 concentric with and covering the needle 56, thereby providing a penetrable seal that substantially prevents the retrograde flow of air into the conduit 32, but facilitates fluid-tight communication between the conduit 32 and the interior 64 of a specimen tube 60 as explained below.

The distal hub 54 preferably has a substantially tapered passage 70 extending axially therethrough, the passage 70 tapering from a distal diameter 70a corresponding substantially to a diameter of the conduit 32 to a proximal diameter 70b corresponding substantially to a diameter of the needle 56. The tapered passage 70 minimizes disruption of a laminar flow characteristic of fluid flowing through the conduit 32 to improve the preferential drawing of fluid from the fluid chamber 30, as discussed below.

The distal hub 52 also preferably has a shape similar to the conduit 32 to facilitate attachment thereof. For example, the distal hub 52 preferably has a slightly tapered shape allowing it to be press fit into a slightly tapered conduit 32, thereby providing a fluid-tight seal and preventing retrograde flow of air into the conduit 32 around the distal hub 52. Alternatively, an adhesive may be applied to the distal hub 52 to seal and/or substantially permanently fix the distal hub 52 in the conduit 32.

The proximal hub 54 preferably has an annular-shaped flange 72 thereon having a size similar to a recess 76 around the proximal opening 48 in the end wall 46. In addition, the proximal hub 54 has an annular portion 74 into which the needle 56 is securely received and onto which the rubber seal 58 is attached. The annular portion 74 may include a harpoon-shaped end (not shown) to facilitate securing the rubber seal 58 thereto and/or to further ensure a fluid-tight seal.

When the distal hub 52 is fixed in the conduit 32, the flange 72 is preferably received in the recess 76 until the flange 72 is substantially flush with the end wall 46. The flange 72 provides additional structural support between the multi-sample luer adapter 50 and the proximal opening 48, particularly against bending stress that may be applied to the needle 56 when a specimen tube 60 is received in the tube-receiving cavity 42. The flange 72 also may further ensure a fluid-tight seal of the proximal opening 48.

The proximal hub 54 thus has a substantially reduced profile which allows the specimen tube 60 to be inserted more fully into the tube-receiving cavity 42, thereby providing improved lateral support for the specimen tube 60 and substantially minimizing bending stress on the needle 56. In an alternative embodiment, the flange 72 on the proximal hub 54 may provide sufficient rigidity that the distal hub 52 may be eliminated (not shown). However, in such an embodiment, it may be necessary to provide an adhesive in the recess 76 to provide a fluid-tight seal and/or prevent removal of the multi-luer adapter 50.

Preferably, the minimized profile of the proximal hub 54 allows the length of the proximal portion 26 to be reduced to facilitate manipulation of the syringe 10 during use. For example, the needle 56 may extend not more than about one inch into the tube-receiving cavity 42. The proximal portion 26 and tube-receiving cavity 42 may then have a length of less than about two inches. A specimen tube 60 may then be received substantially in the tube-receiving cavity 42 before engaging the needle 56, thereby minimizing bending stress on the multi-sample luer adapter 50, and particularly on the hub 52.

The materials of the cylindrical body 12, the plunger assembly 20, and the multi-sample luer adapter 50 are conventional and should be familiar to those skilled in the art. Preferably, the distal and proximal portions 25, 26 of the plunger assembly 20 are formed as a unitary element, for example from injection molded plastic. The piston 22 generally comprises a flexible substantially resilient material, such as thermoplastic rubber (commonly known as Sarlynk), for sealably engaging the interior wall 18 of the cylindrical body 12 in a substantially fluid-tight manner, and facilitating manipulation of the plunger assembly 20 proximally and distally by overcoming a relatively slight frictional resistance resulting from the engagement of the piston 22 and the interior wall 18.

During use, the needle 80 of the syringe 10 is generally percutaneously introduced into a patient (not shown) using conventional methods, although alternatively it may be connected to an indwelling catheter (not shown) previously introduced into a patient. The plunger assembly 20 may be initially directed proximally, drawing blood through the hypodermic needle 80 and the distal opening 17 into the fluid chamber 30. A conventional vacuum specimen tube 60 may be inserted into the tube-receiving cavity 42 in the proximal portion 26 of the plunger assembly 20 until the stopper 62 on the specimen tube 60 and the rubber seal 58 are punctured by the needle 56. Thus, a substantially fluid-tight passage is provided between the hypodermic needle 80, the distal opening 17, the fluid chamber 30, the conduit 32, the needle 56, and the interior 64 of the specimen tube 60.

Because the interior 64 of the specimen tube 60 has a fixed initial low pressure, it imposes a sudden proximal pressure and force on the conduit 32 when it is inserted into the tube-receiving cavity 42, drawing blood into the specimen tube 60 from the conduit 32. Because of the flow induced by the vacuum, the low pressure is translated to the fluid chamber 30.

When the hypodermic needle 80 has a substantially small diameter, or when the indwelling catheter (not shown) is relatively long, it may impose a substantial strain on blood flowing into the distal opening 17. Because the frictional resistance between the piston 22 and the interior wall 18 of the cylindrical body 12 is generally substantially lower than the viscous resistance to flow through the hypodermic needle 80 and the distal opening 17, the pressure from the vacuum tube 60 preferentially draws fluid from the fluid chamber 30. This creates a pressure against the piston face 28 which resists proximal movement of the plunger assembly 20, and/or draws the plunger assembly 20 distally as fluid is drawn from the fluid chamber 30 into the conduit 32.

As the specimen tube 60 is filled, the pressure decreases, allowing additional fluid to slowly enter through the distal opening 17, minimizing the strain on the fluid as it is drawn through the hypodermic needle 80. If additional fluid needs to be drawn into the fluid chamber 30 from the patient, the operator of the device may overcome the deceleration of the plunger assembly 20 and draw the plunger assembly 20 proximally.

Thus, a syringe 10 in accordance with the present invention allows health professionals to control more directly the effects of the low pressure from the initial vacuum of the specimen tube 60, and to substantially minimize the likelihood of hemolysis occurring when blood samples are obtained from a patient. This advantage is obtained because the syringe 10 includes a reservoir, the fluid chamber 30, from which blood is preferentially drawn into the conduit 30 and subsequently into the specimen tube 60. This reduces the amount of blood that must pass through the distal opening 17, reducing the strain and hemolysis that may occur therein. Consequently, a smaller gauge hypodermic needle 80 may be connected to the hub 17, for example to facilitate peripheral access into a patient, without substantially risking increased strain and hemolysis of the blood flowing therethrough. Additional explanation of the fluid mechanics involved in the use of a syringe in accordance with the present invention may be found in the co-pending application Ser. No. 08/797,091, filed on Feb. 2, 1997, the disclosure of which is expressly incorporated herein by reference.

This preferential flow from the fluid chamber 30 to minimize hemolysis may be further enhanced in a number of ways. For example, a restriction, such as an annular projection (not shown), may be provided in the distal opening 17 to increase the viscous resistance of flow through the hub 13. The interior of the hypodermic needle 80 or indwelling catheter (not shown) may then be subjected to lower pressure, thereby reducing the strain on the blood therein.

Alternatively, the lengths and diameters of the needle 80 may be adjusted, particularly in relation to the needle 56 on the multi-sample luer adapter 50, to provide a predetermined viscous resistance to flow through the distal opening 17. For example, if the length of the needle 80 is increased and/or the diameter of the needle 80 is decreased, the viscous resistance to flow therethrough may be increased. This viscous resistance to flow may be set at a value substantially greater than the frictional resistance between the piston 22 and the interior wall 18 of the cylindrical body 12.

In addition, the viscous resistance to flow through the conduit 32 and the needle 56 of the multi-sample luer adapter 50 may be decreased to further enhance the preferential drawing of blood from the fluid chamber 30. This may be achieved by increasing the diameter and/or reducing the length of the conduit 30 and/or the needle 56. Further, however, even if the distal needle 80 and the needle 56 of the multi-sample luer adapter 50 were to have the same lengths and diameters, fluid would still be drawn preferentially from the fluid chamber 30, given that the frictional resistance between the piston 22 and the interior wall 18 of the cylindrical body 12 is substantially less than the viscous resistance to flow through the distal needle 80.

Increasing the diameter of the conduit 32, however, may increase the initial flash of blood, that is the uncontrolled flow of blood into the conduit 32 when the syringe 10 is first introduced into a patient due to the compressibility of air in the conduit 32. In addition, increasing the volume of air in the conduit 32 may also distort the results of certain tests. Therefore, the cross-section or diameter of the conduit 32 is preferably substantially narrow to minimize the volume of air therein. The needle 56, however, may be decreased in length and/or increased in diameter to provide a desired reduction in viscous resistance of flow.

For example to obtain a ratio of desired viscous resistances to flow, the needle 80 may have an inner diameter of about 0.021 inches or less and a length of about 1.0 inch or more, while the needle 56 may have an inner diameter of not more than about 0.0245 inches and a length of not more than about 1.05 inches. This can provide a desired ratio of viscous resistance to blood flow into the fluid chamber 30 from the needle 80 and distal opening 17, and out of the fluid chamber 30 into the conduit 32 and needle 56.

To further appreciate the preferential flow conditions achieved with a syringe in accordance with the present invention, a discussion of the general physics and fluid dynamics related to the present invention is required. Pressure P is defined as a given force F distributed over a unit of area A, that is:

$$P = F/A. \tag{1}$$

From equation (1), because force equals a mass under acceleration, the observed pressure within any syringe in use is shown to be simply a function of the acceleration a (or change in velocity over time, dv/dr) of the piston-plunger assembly in a proximal or distal direction times its fixed mass m. This acceleration is generally imparted by the technical skills of the health professional. Thus, the above principles show that a syringe of any volume, having a hypodermic needle attached to its distal end, will cause a fluid to experience an acceleration equal in magnitude and direction to the acceleration experienced by the piston-plunger assembly.

When considering blood flow, the laws governing non-Newtonian viscous fluids apply. By definition, viscosity f is that inherent property of a fluid that resists motion, i.e. flow, and has units of mass, length, and time. According to Poiseuille's Law:

$$Q = \Delta P \pi R^4 / 8 \eta l. \tag{2}$$

Poiseuille's Law determines that the flow Q of a viscous fluid is directly proportional to a pressure drop $\Delta P$ and the fourth power of the radius of the flow tube. In the case of whole blood collection with a vacuum specimen tube, $\Delta P$ is constant and cannot otherwise be manipulated. Clearly then, an observed net 22 flow of blood with viscosity $\eta$ into a vacuum tube is more a reflection of the surface area of the hypodermic needle having a radius r and a length l. Recognizing this, the viscous force that a pressure drop $\Delta P$ must overcome to observe a net flow of viscous blood is:

$$F = -\eta A dv/dr \tag{3}$$

where A is the surface area of the needle and dv/dr is the acceleration required. Therefore, the net driving force through a cylindrical tube having a radius r subjected to a pressure $\Delta P$ is $\Delta P \pi r^2$, which may be equated to the viscous force in equation (3) required to cause flow of the fluid, namely:

$$\Delta P \pi r^2 = \eta A dv/dr. \tag{4}$$

Because the pressure value $\Delta P$ is constant and fixed by the vacuum tube, equation (4) can be solved for velocity:

$$dv = \Delta P \pi r^2 dr / \eta A. \tag{5}$$

With the surface area of the needle being that of a cylinder, namely $2\pi r l$, this becomes:

$$dv = \Delta P r dr / 2 \eta l \tag{6}$$

Integrating both sides gives:

$$\int_v^0 dv = \Delta P/2\eta l \int_r^R r\, dr, \tag{7}$$
$$v = \Delta P/4\eta l (R^2 - r^2).$$

Equation (7) shows that a maximum velocity $v_{max}$ results when r equals zero. In this equation, R is the radius of the diameter of the hypodermic needle and r is the radius of a thin cylindrical shell of viscous blood flowing through the hypodermic needle. Intuitively, it can be realized that laminar flow results in a long, narrow cylindrical tube, establishing a velocity gradient. This velocity gradient varies from zero along the inner wall of the hypodermic needle and increases to $v_{max}$, in the central portion of the blood flow. Maximum velocity of the blood occurs when r equals zero. Velocity approaches zero as r approaches R. Again, this variation in velocity is a consequence of laminar flow of a viscous fluid.

As a viscous fluid travels through a flow tube, it experiences a pressure drop due to the viscous losses through the tube. The viscosity of the fluid resists flow, with the greatest amount of resistance occurring along the inner wall of the flow tube where the velocity is essentially zero (v=0, r=R). The least amount of resistance occurs in the central portion of the fluid flow where the velocity is maximized (v=$v_{max}$, r=0). The integral v=0 to v=$v_{max}$ shows that the blood flow occurs in various thin cylinders of fluid at a given r, forming the basis for laminar flow. Thus, solving for the maximum velocity in equation (7) gives:

$$v_{max} = \Delta P R^2 / 4\eta l. \tag{8}$$

This equation is of particular interest when applied to a syringe in accordance with the present invention. The present invention provides a syringe for receiving fixed vacuum specimen tubes that results in a preferential drawing of fluid from the fluid chamber, resulting in automatic advancement of the piston-plunger assembly after a sample of blood has been initially aspirated into the barrel of the syringe. For this preferential flow to occur, there must be a difference in fluid velocities through the flow tubes extending into and out of the fluid chamber, i.e. into the distal flow tube (e.g. the needle 80 of FIG. 1) and out the proximal flow tube (e.g. the conduit 32 and the collection needle 56 of the multi-sample luer adapter 50, as shown in FIG. 1). For each of these flow tubes, the maximum velocity is defined as:

$$V_{max} = \Delta P R_1^2 / 4\eta l_1 \quad (9)$$

$$V_{max} = \Delta P R_2^2 / 4\eta l_2 \quad (10)$$

where Equation (9), which includes $R_1$ as the radius of the distal flow tube and $l_1$ as its length, represents flow into the fluid chamber, and where Equation (10) represents flow out of the fluid chamber through the proximal flow tube. Given that Equations (9) and (10) represent a maximum flow velocity, an inequality may be established such that the flow out the proximal end is greater than that into the distal end when preferential flow occurs to give:

$$\Delta P R_1^2 / 4\eta l_1 << \Delta P R_2^2 / 4\eta l_2. \quad (11)$$

Elimination of the fixed variables provides:

$$R_1^2 / l_1 << R_2^2 / l_2 \quad (12)$$

Equation (12) shows that the velocity of fluid flow at the distal and proximal ends of the syringe are directly related to the ratios of the respective radii and lengths of their flow tubes, with the flow through the proximal end being greater than the flow through the distal end. Specifically, one may further determine the ratio of one flow tube radius to the other given equal lengths of the flow tubes:

$$R_1^2 / R_2^2 << l_2 / l_2, \text{ or} \quad (13)$$

$$R_1^2 / R_2^2 << 1. \quad (14)$$

It is apparent in Equation (14) above that for a significant difference in velocity to exist between the proximal and distal ends of the syringe, the ratio of the respective radii must be substantially less than 1 when the respective lengths are substantially the same. Furthermore, when the length and radius of the proximal flow tube are both varied as compared to the distal end, Equation (12) applies. This substantial difference in flow velocity between the proximal and distal ends of the syringe generates a differential pressure within the fluid chamber.

This differential pressure generates a residual force that acts directly on the piston and thereby induces the preferential proximal flow of fluid from the syringe barrel. This residual force is realized through the proximal advancement of the piston-plunger assembly. We can define and determine the character of this residual force as follows:

$$R_1^2 / (R_1 + r)^2 << 1 \quad (15)$$

where $R_2^2$ is the sum of the distal radius $R_1$ plus a small increase in radius r quantity squared. Poiseuille's law (Equation (2) above), shows the following:

$$Q_p = \Delta P \pi R_p^4 / 8\eta l \quad (16)$$

in which $Q_p$ is the fluid flow at the proximal end of the syringe, i.e. through the collection needle, and $R_p$ is ($R_1$+r). $\Delta P$ is given by the vacuum tube and is realized over the length l of the collection needle.

It should be appreciated that as fluid is transferred to the vacuum tube, the $\Delta P$ acting over the collection needle diminishes until the pressure within the vacuum tube is substantially equal to the pressure within the fluid chamber.

When considering the velocity of flow within the fluid chamber, the continuity equation applies, namely:

$$v_{avg-s} A_s = V_{avg-p} A_p \quad (17)$$

to give:

$$V_{avg} = Q_p / A_s \quad (18)$$

where $A_s$ is the area of fluid in contact with the piston face, and $A_p$ is the area of fluid traveling within the collection needle. In Equation (18), $V_{avg}$ is the average velocity of fluid flow within the syringe barrel, and $Q_p$ is the flow rate of fluid through the collection needle.

It should be appreciated that $Q_p$ will diminish as $\Delta P$ diminishes, and thus, the average velocity $V_{avg}$ of fluid flow within the fluid chamber will decrease through the continuity equation as shown above. Using the equation for maximum velocity, it can be determined that the differential pressure dP within the fluid chamber is as follows:

$$V_{max} = \Delta P R^2 / 4\eta l \quad (19)$$

$$dP(\Delta P) = -2 v_{avg} 4\eta l_s / R_s^2 \quad (20)$$

$$dP = -8k v_{avg} / R_s^2 \quad (21)$$

where k is the product of the fluid viscosity $\eta$ and the length $l_s$ of the fluid sample within the fluid chamber, and $R_s$ is the radius of the cylindrical fluid chamber. Further, recall that average velocity is equal to ½ $v_{max}$. The negative sign indicates that the pressure within the barrel of the syringe is less than atmospheric pressure, i.e. a vacuum is generated. Recall from Equation (1) that pressure P equals force F over area A. Equating this to Equation (21) yields:

$$F/A_s = -8k v_{avg} / R_s^2 \quad (22)$$

$$F_r = -8k v_{avg}. \quad (23)$$

Clearly, the residual force Fr acting on the piston face is directly proportional to the average velocity of the fluid flow out of the fluid chamber. The negative sign indicates that the direction of this residual force is opposite to the direction of the fluid flow. This force $F_r$ can only be maximized through a large flow rate $Q_p$ at the proximal collection needle as shown in Equation (18) above.

The prevention of hemolysis results principally from the preferential draw of fluid from the fluid chamber. Fluid will generally be drawn from the fluid chamber if two criteria are met: (1) the residual force acting on the piston face is greater than the frictional force between the piston and the inner wall of the syringe barrel, and (2) this frictional force is less than the viscous resistance to flow at the syringe tip. The force equations that govern are as follows:

$$F = -\eta A dv / dr, \quad (3)$$

$$F_r = -8k v_{avg}, \text{ and} \quad (23)$$

$$f = -\mu N. \quad (24)$$

where Equation (3) is the viscous resistance to flow at the syringe tip, Equation (23) is the force acting on the piston face, and Equation (24) is the frictional force between the piston and the inner wall of the syringe barrel, and where $\mu$ is the coefficient of friction and N is the normal force of the piston-plunger assembly.

Clearly, to minimize hemolysis of red blood cells, the preferential draw of blood from the fluid chamber must be ensured. In order to maximize the preferential draw of fluid from the fluid chamber, the flow $Q_p$ as in Equation (18) must be maximized. Thus, the functional limits of the residual force $F_r$ of Equation (23) are as follows:

$$-\eta A dv/dr > \mu N < -8kv_{avg}. \quad (25)$$

Thus, when the piston is in its proximal position, as long as the frictional force is less than the other forces (i.e. the viscous resistance to flow at the syringe tip and the viscous force to achieve flow of blood), fluid will be preferentially drawn from the fluid chamber into the specimen tube.

To summarize, when a vacuum specimen tube is inserted into conventional double needle devices, the pressure from the initial vacuum in the specimen tube is exerted onto the fluid in the rear needle. Blood travels proximally through the rear needle into the specimen tube, applying a similar pressure on blood within the front needle. However, because the front needle may have a smaller cross-section, the pressure imposes a greater strain on the fluid traveling therethrough. This increased strain on the blood flowing through the narrow needle increases the likelihood of hemolysis of the blood, providing less desirable blood samples.

In contrast, the present invention includes a reservoir, the fluid chamber, from which blood is drawn into the conduit and subsequently into the specimen tube. This reduces the amount of blood that must pass through the distal opening, reducing the strain and hemolysis that may occur therein. This preferential flow from the fluid chamber also decelerates the proximal movement of the plunger assembly, and creates a pressure resistance, thereby reducing the pressure to which blood in the hypodermic needle is exposed. Thus, a smaller gauge needle may be connected to the hub without substantially risking increased strain and hemolysis of the blood flowing therethrough.

An additional feature of the present invention is that the tube-receiving cavity 42 is formed directly in the plunger assembly 20, rather than requiring attachment of a separate tube-holding device to the conduit 32. The tube-receiving cavity 42 protects the multi-sample luer adapter 50, while the multi-sample luer adapter 50 ensures that the fluid chamber 30 and conduit 32 remain substantially sealed throughout the use of the syringe 10, further ensuring preferential drawing of fluid from the fluid chamber 30. A detachable seal and/or tube-holding device may expose the conduit 32 and any fluid therein to contaminants, for example to the retrograde flow of air into the conduit, which may distort test results.

Thus, when a specimen tube 60 is inserted into the tube-receiving cavity 42, it communicates through the needle 56 and the proximal opening 48 directly with the conduit 32 and thereby is substantially sealed from exposure to air or other contaminants. The tube-holding cavity 42 is not detachable from the plunger assembly 20, and so cannot inadvertently detach when the plunger assembly 20 is manipulated, for example when the plunger assembly 20 is initially drawn proximally to fill the fluid chamber 30, or when blood samples are being drawn into a series of specimen tubes.

Further, the tube-receiving cavity 42 substantially protects the multi-sample luer adapter 50 throughout use of the syringe 10. For example, the multi-sample luer adapter 50 is not easily accessible and so may not be intentionally or inadvertently removed from the proximal opening 48, which may eject fluid from the conduit 32 and/or expose the fluid therein to contaminants. In addition, the multi-sample luer adapter 50, and in particular the distal hub 52 and needle 56, are subjected to minimal stress during use of the syringe 10, preventing risk of damage to the multi-sample luer adapter 50, and further ensuring preferential drawing of fluid from the fluid chamber 30. For example, because the plunger assembly 20 is a unitary member, no bending stresses are applied to the distal hub 52 of the multi-sample luer adapter 50 during manipulation of the syringe 10, as may be imposed on a separate tube-holding device. When a specimen tube 60 is inserted into the tube-receiving cavity 42, the cylindrical shape of the tube-receiving cavity 42 may also minimize bending stress which may damage the needle 56 by aligning the specimen tube 60 substantially axially with the needle 56.

Figure 3:
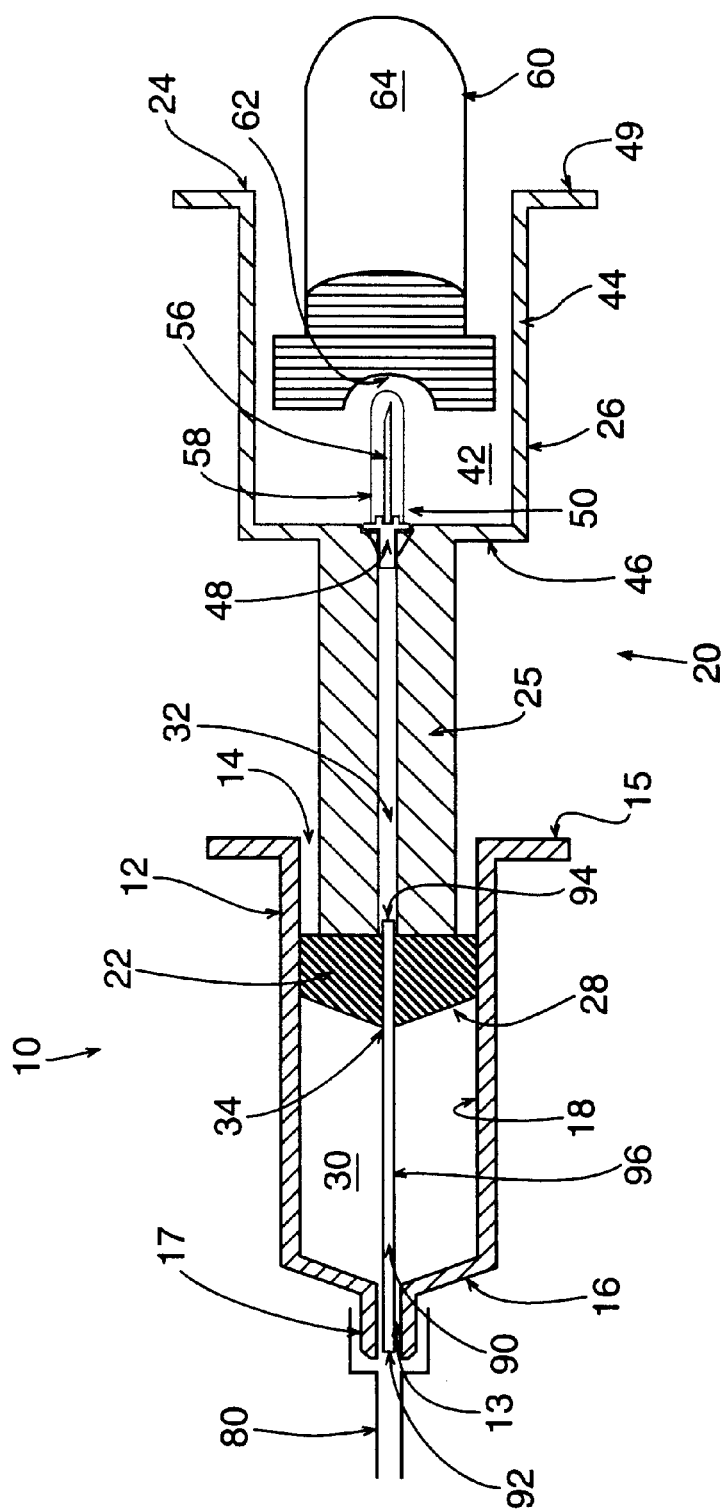
FIG. 3 is a cross-section of a second preferred embodiment of a syringe in accordance with the present invention, having an inner cannula for substantially separating the fluid chamber from the conduit in the plunger assembly.

Turning now to FIG. 3, a second preferred embodiment of the present invention is shown, namely a syringe 10, similar to that previously described, which includes a substantially cylindrical body 12, a plunger assembly 20, and a multi-sample luer adapter 50. In addition, the syringe 10 includes an inner cannula 90, having a distal end 92 and a proximal end 94. The distal end 92 is disposed adjacent the distal opening 17, preferably extending partially into the hub 13 on the distal end 16 of the cylindrical body 12.

The inner cannula 90 generally has an outer cross-section smaller than the distal opening 17, thereby allowing fluid to pass around the inner cannula 90 between the distal opening 17 and the fluid chamber 30. The inner cannula 90 is also preferably supported at its distal end 92 by a plurality of struts or ribs (not shown) extending between the outer surface 96 of the inner cannula 90 and the inner wall of hub 13.

The proximal end 94 of the cannula 90 communicates with the conduit 32 passing through the plunger assembly 20. Preferably, the inner cannula 90 extends into the opening 34 in the piston face 28, and the piston 22 slidably engages the outer surface 96 of the cannula 90, thereby substantially sealing the conduit 32 from the fluid chamber 30. Thus, fluid may communicate either between the distal opening 17 and the fluid chamber 30, or between the distal opening 17 and the conduit 32, the fluid chamber 30 and the conduit 32 remaining substantially separate from each other.

Similar to the method of use described above, the needle 80 of the syringe 10 may be percutaneously introduced into a patient, or may be attached to an indwelling catheter (not shown). The plunger assembly 20 may be directed proximally, drawing fluid through the distal opening 17 into the fluid chamber 30. Once a desired first fluid sample is contained within the fluid chamber 30, a vacuum specimen tube 60 may be inserted into the tube-receiving cavity 42. The vacuum within the interior 64 of the specimen tube 60 draws fluid from the patient through the distal end 92 of the cannula 90, through the conduit 32, and into the specimen tube 60.

Because the distal end 92 is fixed in the distal opening 17, the specimen tube 60 draws a second fluid sample directly from the patient, rather than from the fluid chamber 30. Thus, the first sample contained in the fluid chamber 30 may be substantially separated from the second and any subsequent samples drawn through the conduit 32, for example into specimen tubes. As described above, because the conduit 32 is substantially sealed throughout use of the syringe 10, a plurality of blood samples may be provided for laboratory testing using the syringe 10 that are substantially uncontaminated and free of hemolysis.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A medical syringe for obtaining a fluid sample from a patient, said medical syringe comprising:
   an elongate body having an interior wall, an open proximal end, and a closed distal end, said distal end having a distal opening therethrough;
   a plunger assembly having unitary proximal and distal portions and being slidably disposed in said proximal end of said elongate body, said distal portion sealably engaging said interior wall, thereby defining a fluid chamber between a distal end of said plunger assembly and said distal end of said elongate body, said proximal portion including a cavity therein for receiving a vacuum specimen tube;
   a conduit extending proximally from said fluid chamber through said distal portion of said plunger assembly to a proximal opening communicating with said cavity in said proximal portion; and
   a penetrable seal in said cavity for substantially sealing said conduit from retrograde flow of air.

2. The syringe of claim 1, wherein said penetrable seal includes a needle attached to said proximal opening and extending into said cavity.

3. The syringe of claim 2, wherein said penetrable seal comprises a rubber seal substantially covering said needle.

4. The medical syringe of claim 1, further comprising a vacuum specimen tube insertable into said cavity and being detachably connectable to said conduit through said penetrable seal.

5. The medical syringe of claim 1, further comprising a cannula extending proximally from said distal opening into said conduit.

6. The medical syringe of claim 5, wherein said cannula extends into said opening in said piston face, said piston sealably engaging said cannula to substantially separate said fluid chamber from said conduit.

7. The medical syringe of claim 1, wherein said plunger assembly comprises injection molded plastic.

8. A medical syringe for obtaining a fluid sample from a patient, said medical syringe comprising: an elongate body having an interior wall, an open proximal end, and a closed distal end, said distal end having a distal opening therethrough;
   a plunger assembly having proximal and distal portions and being slidably disposed in said proximal end of said elongate body, said distal portion sealably engaging said interior wall, thereby defining a fluid chamber between a distal end of said plunger assembly and said distal end of said elongate body, said proximal portion including a cavity therein for receiving a vacuum specimen tube;
   a conduit extending proximally from said fluid chamber through said distal portion of said plunger assembly to a proximal opening communicating with said cavity in said proximal portion; and
   a penetrable seal in said cavity for substantially sealing said conduit from retrograde flow of air, wherein said penetrable seal comprises a multi-sample luer adapter sealably attached to said opening.

9. The syringe of claim 8, wherein said multi-sample luer adapter comprises a hub adapted to be at least partially directed into said conduit.

10. A medical syringe for obtaining a fluid sample from a patient, said medical syringe comprising:
    an elongate body having an interior wall, an open proximal end, and a closed distal end, said distal end having a distal opening therethrough:
    a plunger assembly having proximal and distal portions and being slidably disposed in said proximal end of said elongate body, said distal portion sealably engaging said interior wall, thereby defining a fluid chamber between a distal end of said plunger assembly and said distal end of said elongate body, said proximal portion including a cavity therein for receiving a vacuum specimen tube;
    a conduit extending proximally from said fluid chamber through said distal portion of said plunger assembly to a proximal opening communicating with said cavity in said proximal portion;
    a penetrable seal in said cavity for substantially sealing said conduit from retrograde flow of air;
    a cannula extending proximally from said distal opening into said conduit, wherein said cannula has a cross-section smaller than said distal opening, thereby allowing a first fluid sample to be drawn into said fluid chamber, and allowing a second fluid sample to be drawn into said conduit.

11. A medical syringe for obtaining a plurality of fluid samples from a patient, said medical syringe comprising:
    a elongate body having an interior wall, an open proximal end, and a closed distal end, said distal end having a distal opening therethrough;
    a hub on said distal end and extending distally therefrom, said distal opening extending distally through said hub;
    a plunger having proximal and distal ends, said plunger having a distal portion slidably disposed in said proximal end of said elongate body, said plunger having an enlarged proximal portion extending proximally beyond said proximal end of said elongate body;
    a piston on said distal end of said plunger, said piston sealably engaging said interior wall of said elongate body, thereby defining a fluid chamber between a piston face of said piston and said distal end of said elongate body;
    a tube-receiving cavity extending distally into said proximal portion from said proximal end of said plunger, said tube-receiving cavity having a size adapted to receive a portion of a vacuum specimen tube therein; a conduit extending proximally from an opening in said piston face through said distal portion of said plunger to a proximal opening in said tube-receiving cavity; and
    a multi-sample luer adapter in said proximal opening, said multi-sample luer adapter including a needle extending proximally from said proximal opening for penetrating a seal on the portion of the vacuum specimen tube received in said tube-receiving cavity, said multi-sample luer adapter having a penetrable seal covering said needle for substantially sealing said conduit from retrograde flow of air.

12. The medical syringe of claim 11, wherein said hub is adapted to receive an indwelling catheter thereon.

13. The medical syringe of claim 11, further comprising a vacuum specimen tube insertable into said tube-receiving cavity for receiving a fluid sample through said conduit.

14. The syringe of claim 11, wherein said tube-receiving cavity has a length less than about two inches, and wherein said needle extends proximally into said tube-receiving cavity from said distal opening less than about one inch, thereby substantially minimizing lateral movement of a vacuum specimen tube received in said tube-receiving cavity.

15. The medical syringe of claim 11, further comprising a hypodermic needle on said hub.

16. The syringe of claim 15, wherein said hypodermic needle and said needle on said multi-sample luer adapter have predetermined lengths and inside diameters adapted to provide predetermined viscous resistances to flow, said viscous resistance to flow through said hypodermic needle being substantially higher than said viscous resistance to flow through said needle on said multi-sample luer adapter, whereby a fluid sample obtained through said conduit is preferentially drawn from said fluid chamber.

17. The medical syringe of claim 16, wherein said hypodermic needle has a length of at least about 1.0 inch and an inside diameter of at least about 0.021 inches, and said needle on said multi-sample luer adapter has a length of not more than about 1.05 inches and an inner diameter of not more than about 0.0245 inches.

18. The medical device of claim 11, wherein said multi-sample luer adapter includes a distal hub disposed at least partially in said conduit, said distal hub having a substantially tapered passage therethrough, said multi-sample luer adapter having a proximal flange engaging said distal opening, thereby substantially minimizing a proximal profile of said multi-sample luer adapter.

19. The medical syringe of claim 18, wherein said substantially tapered passage has a distal diameter corresponding substantially to a diameter of said conduit, and has a proximal diameter corresponding substantially to a diameter of said needle, thereby minimizing disruption of a laminar flow characteristic through said distal hub.

20. The medical syringe of claim 18, wherein said distal hub sealably engages said conduit, thereby substantially preventing retrograde flow of air into said conduit around said hub.

21. The medical syringe of claim 18, wherein said distal hub is press fit into said conduit.

* * * * *